US007621892B2

(12) United States Patent
Fago et al.

(10) Patent No.: US 7,621,892 B2
(45) Date of Patent: Nov. 24, 2009

(54) CONTRAST CONTAINER HOLDER AND METHOD TO FILL SYRINGES

(75) Inventors: Frank Fago, Mason, OH (US); Robert Bergen, Westchester, OH (US); James F. Farmer, Mantua, NJ (US)

(73) Assignee: Mallinckrodt Inc., Hazelwood, MO (US)

( * ) Notice: Subject to any disclaimer, the term of this patent is extended or adjusted under 35 U.S.C. 154(b) by 425 days.

(21) Appl. No.: 10/750,427

(22) Filed: Dec. 31, 2003

(65) Prior Publication Data
US 2005/0148868 A1 Jul. 7, 2005

(51) Int. Cl.
*A61M 1/00* (2006.01)
(52) U.S. Cl. .................. 604/151; 604/152; 604/208; 604/218; 604/181; 604/187
(58) Field of Classification Search .................. 141/237; 604/151, 236, 152, 246–247, 500, 280–283, 604/181, 187, 183–184; 600/432
See application file for complete search history.

(56) References Cited

U.S. PATENT DOCUMENTS

| 4,065,230 | A | | 12/1977 | Gezari | |
|---|---|---|---|---|---|
| 4,562,829 | A | | 1/1986 | Bergner et al. | |
| 5,034,004 | A | | 7/1991 | Crankshaw | 604/154 |
| 5,298,023 | A | | 3/1994 | Haber et al. | |
| 5,334,162 | A | | 8/1994 | Harris et al. | |
| 5,425,716 | A | | 6/1995 | Kawasaki et al. | 604/152 |
| 5,456,669 | A | | 10/1995 | Neer et al. | 604/154 |
| 5,573,515 | A | * | 11/1996 | Wilson et al. | 604/236 |
| 5,662,612 | A | | 9/1997 | Niehoff | 604/155 |
| 5,800,397 | A | | 9/1998 | Wilson et al. | |
| 5,868,710 | A | | 2/1999 | Battiato et al. | 604/123 |
| 5,925,022 | A | * | 7/1999 | Battiato et al. | 604/208 |
| 6,471,674 | B1 | | 10/2002 | Emig et al. | |
| 2001/0018935 | A1 | | 9/2001 | Castellano | |
| 2001/0047153 | A1 | | 11/2001 | Trocki et al. | |
| 2002/0068905 | A1 | | 6/2002 | Cowan et al. | |

(Continued)

FOREIGN PATENT DOCUMENTS

EP          1323446 A        7/2003

(Continued)

OTHER PUBLICATIONS

Medrad, Inc., "Stellant CT Injection System", Operation Manual Catalog #SOM 700 EN, 2003, 88 pages.

(Continued)

*Primary Examiner*—Nicholas D Lucchesi
*Assistant Examiner*—Quynh-Nhu H Vu
(74) *Attorney, Agent, or Firm*—Wood Herron & Evans LLP

(57) ABSTRACT

The filling of a syringe can be performed at a faster rate using a filling sequence which expels air from the fill tube before filling the syringe. A similar method is used when changing contrast containers during a filling sequence to ensure that all the air is expelled from the fill tube before filling resumes with the new contrast container. Additionally, by including a contrast container holder that is affixed to an injector head and holds the container near the syringe tip, the filling sequence can be accomplished without requiring the operator to hold the contrast container during the sequence.

83 Claims, 5 Drawing Sheets

U.S. PATENT DOCUMENTS

| | | | |
|---|---|---|---|
| 2004/0024361 A1* | 2/2004 | Fago et al. | 604/152 |
| 2004/0133165 A1* | 7/2004 | Duchon et al. | 604/151 |
| 2004/0158205 A1* | 8/2004 | Savage | 604/151 |

FOREIGN PATENT DOCUMENTS

| | | |
|---|---|---|
| WO | WO0204049 A | 1/2002 |
| WO | WO0207812 A | 1/2002 |
| WO | WO02087663 A | 11/2002 |
| WO | 2007/133942 A2 | 11/2007 |
| WO | 2007/133942 A3 | 11/2007 |

OTHER PUBLICATIONS

Chinese App No. 2004800396111 / Office Action mailed Jul. 4, 2008 and English Translation.

Chinese App No. 2004800396111 / Office Action mailed Mar. 20, 2009 and English Translation.

European App No. 04 813 537.0 - 1257 / Office Action mailed Sept 29, 2008.

* cited by examiner

CONTRAST CONTAINER HOLDER AND METHOD TO FILL SYRINGES

FIELD OF THE INVENTION

The present invention relates to injectors for injecting fluid into patients.

BACKGROUND OF THE INVENTION

In many medical environments, a medical fluid is injected into a patient during diagnosis or treatment. One example is the injection of contrast media into a patient to improve Optical Imaging, Nuclear Medicine, CT, Angiographic, Magnetic Resonance or Ultrasound imaging, or any diagnostic imaging or therapeutic application using a powered, automatic injector.

Injectors suitable for these and similar applications typically must use a relatively large volume syringe and be capable of producing relatively large flow rates and injection pressures. For this reason, injectors for such applications are typically motorized, and include a large, high mass injector motor and drive train. For ease of use, the motor and drive train are typically housed in an injection head, which is supported by a floor, wall, or ceiling mounted arm.

The injection head is typically mounted on the arm in a pivotal manner, so that the head may be tilted upward (with the syringe tip above the remainder of the syringe) to facilitate filling the syringe with fluid, and downward (with the syringe tip below the remainder of the syringe) for injection. Tilting the head in this manner facilitates removal of air from the syringe during filling, and reduces the likelihood that air will be injected into the subject during the injection process. Nevertheless, the potential for accidentally injecting air into a patient remains a serious safety concern.

In addition to the injection head discussed above, many injectors include a separate console for controlling the injector. The console typically includes programmable circuitry which can be used for automatic, programmed control of the injector, so that the operation of the injector can be made predictable and potentially synchronized with operations of other equipment such as scanners or imaging equipment.

One particular operational routine performed by the injector system is that of filling the syringe with contrast. This filling sequence for a power injector typically requires the use of both hands by the operator. A contrast container is held in one hand in close proximity to the injector while the other hand operates the injector controls to retract the plunger so as to fill the syringe. Even in injectors which can auto-fill a preset volume, the use of both hands by the operator is still required when initially starting the auto-fill sequence.

Accordingly, a need exists to simplify the syringe sequence in power injectors so that an operator can have at least one hand available to perform other activities during the entire operation of filling a syringe.

Occasionally when filling a syringe, the filling sequence can be problematic in that if it is performed too fast, the contrast media is aerated or if it is performed too slow, the sequence can take an unreasonable amount of time to complete. There is, therefore, based on the contrast media and the possible presence of air in the fill tube, a maximum filling rate for contrast media that will avoid aerating the contrast media during filling. While this speed can be programmed in the injector and automatically used, an operator typically monitors the syringe filling to further reduce the likelihood of aeration of the contrast media. A need exists for a filling sequence that permits filling of the syringe with contrast fluid faster than the maximum filling speed attainable if air is present in the fill tube.

SUMMARY OF THE INVENTION

Those needs identified above and other problems of conventional injector systems are addressed by embodiments of the present invention that permit hands-free filling of a syringe and by embodiments that perform a filling sequence without aerating the contrast media during filling.

One aspect of the present invention relates to a contrast media injector system that includes an injector head and a contrast container holder connected with the injector head, wherein the contrast container holder is configured to hold a contrast container in a substantially fixed position while the injector head is oriented substantially vertical.

Still a further aspect of the present invention relates to a method for performing a filling sequence in a contrast media injector system having a fill tube coupling a syringe to a contrast media. In accordance with this aspect, substantially all air is expelled from the fill tube and, thereafter, the syringe is filled at a first rate wherein aeration of the contrast media is prevented and wherein the first rate is faster than a second rate that is a maximum fill rate if air is not previously expelled from the fill tube.

One more aspect of the present invention relates to a method for changing contrast media containers during a syringe filling sequence. In accordance with this aspect, the syringe filling sequence of a syringe is paused when a first contrast container is substantially emptied and the first contrast container is replaced with a second contrast container. Next, substantially all air is expelled from a fill tube coupled between the syringe and the second contrast container and, thereafter, filling of the syringe from the second contrast container is resumed at a first rate wherein aeration of the contrast media is prevented and wherein the first rate is faster than a second rate that is a maximum fill rate if air is not previously expelled from the fill tube.

DETAILED DESCRIPTION OF THE INVENTION

Motorized Injection Systems

Figure 1:
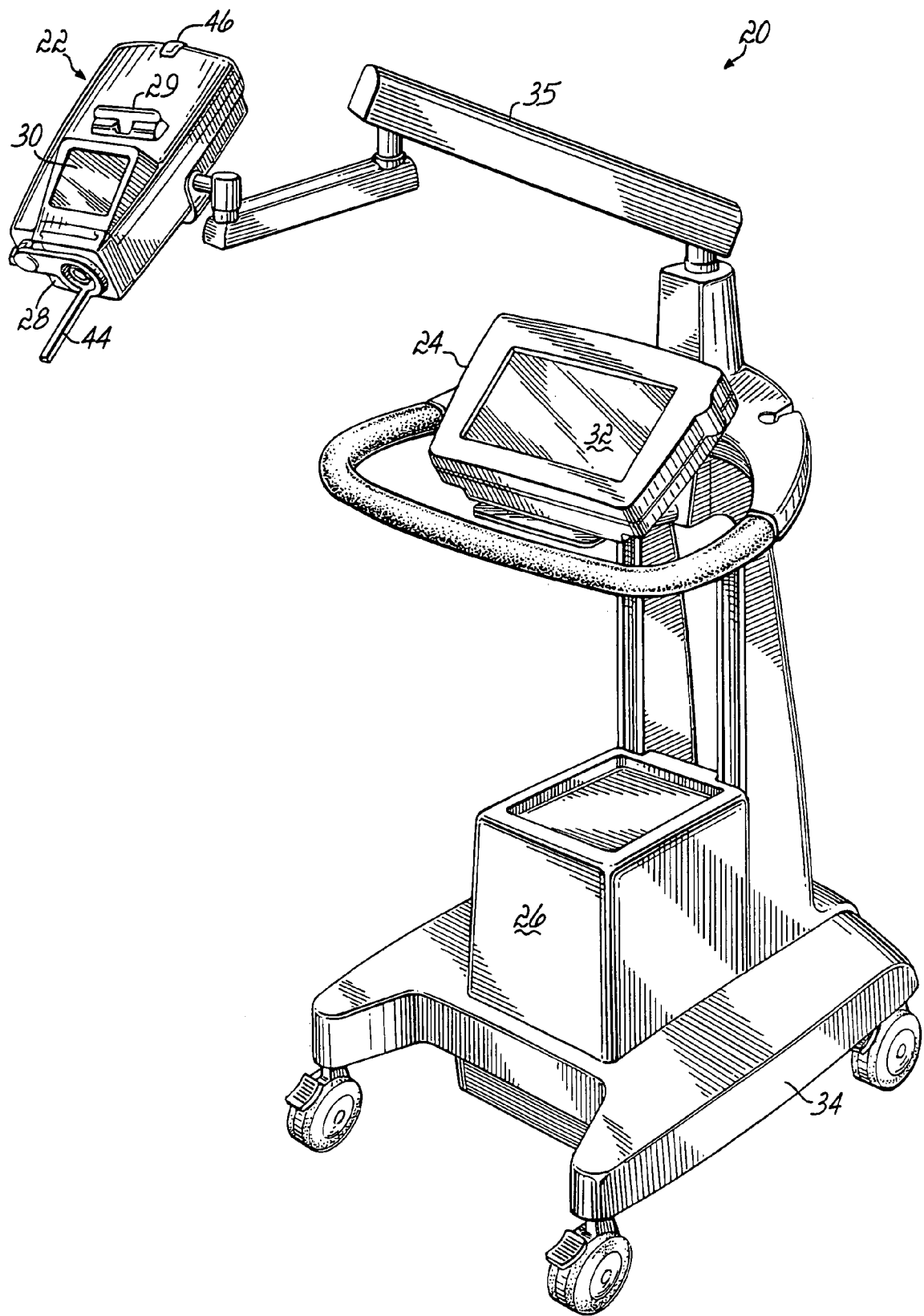
FIG. 1 illustrates a perspective view of an injector in accordance with principles of the present invention, including a power head, console, and power pack (under a cover), with the syringe, pressure jacket, heater blanket and air detection module removed.

Referring to FIG. 1, an injector 20 in accordance with the present invention includes various functional components, such as a power head 22, a console 24 and power pack 26 (mounted inside of a cover). A syringe 36 (FIG. 2) is mounted to the injector 20 in the face plate 28 of the power head 22, and the various injector controls are used to fill the syringe with, e.g., contrast media for a CT, Angiographic or other procedure, which media is then injected into a subject under investigation under operator or pre-programmed control.

The injector power head 22 includes a hand-operated movement control lever 29 for use in controlling the movement of the internal drive motor, and a display 30 for indicating to the operator the current status and operating parameters of the injector. The console 24 includes a touch screen display 32 which may be used by the operator to remotely control operation of the injector 20, and may also be used to specify and store programs for automatic injection by the injector 20, which can later be automatically executed by the injector upon initiation by the operator.

Power head 22 and console 24 connect through cabling (not shown) to the power pack 26. Power pack 26 includes a power supply for the injector, interface circuitry for communicating between the console 24 and power head 22, and further circuitry permitting connection of the injector 20 to remote units such as remote consoles, remote hand or foot control switches, or other original equipment manufacturer (OEM) remote control connections allowing, for example, the operation of injector 20 to be synchronized with the x-ray exposure of an imaging system Power head 22, console 24 and power pack 26 are mounted to a carriage 34 which includes a support arm 35 for supporting power head 22 for easy positioning of power head 22 in the vicinity of the examination subject. Other installations are also contemplated however; for example, console 24 and power pack 26 may be placed on a table or mounted on an electronics rack in an examination room while power head 22 is supported by a ceiling, floor or wall mounted support arm.

Figure 2:
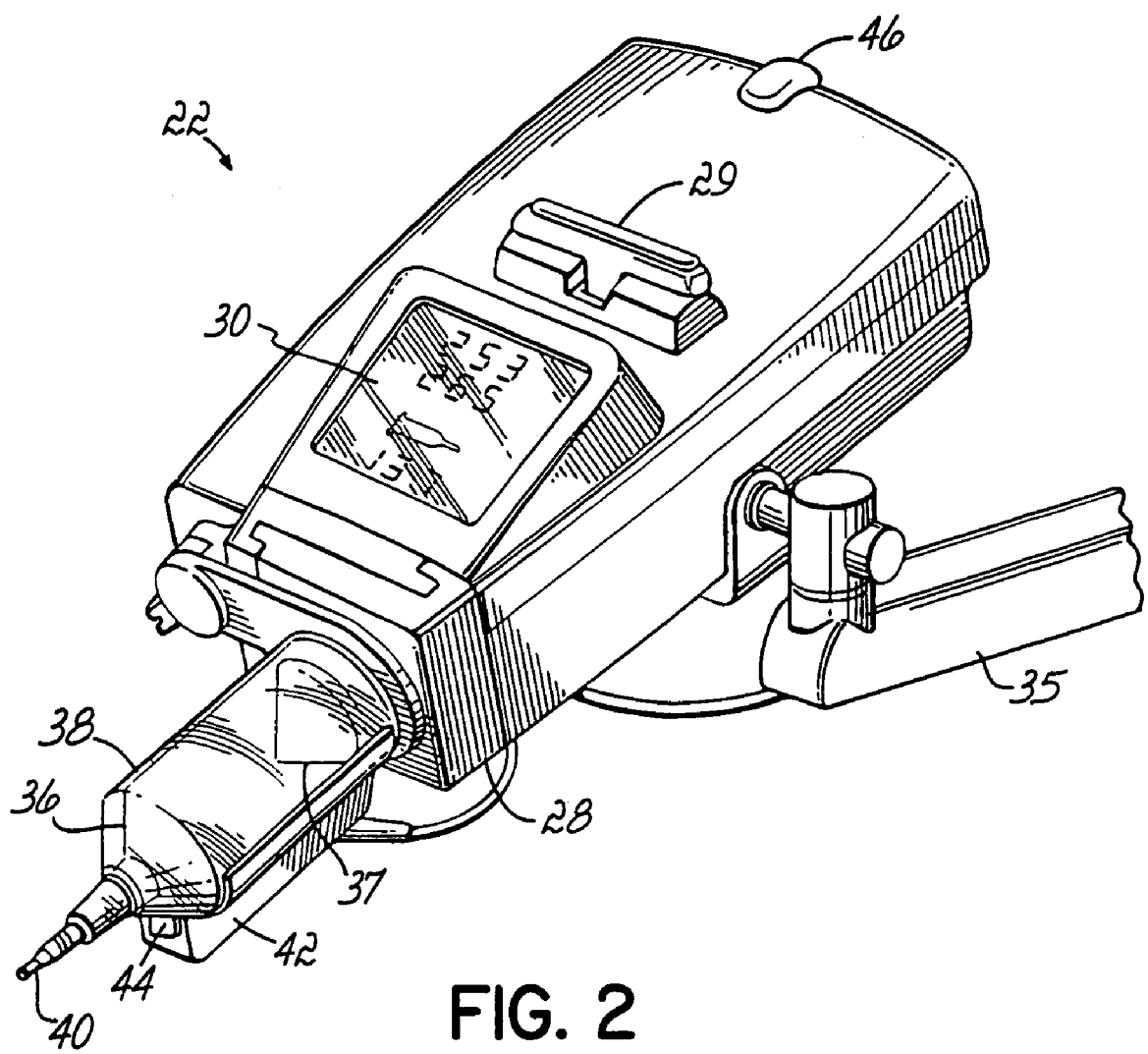
FIG. 2 illustrates a perspective view of the power head of the injector of FIG. 1 with a pressure jacket, syringe and heater blanket mounted thereto, showing the power head display, hand-operated control, and support arm mounting in greater detail.

Referring now to FIG. 2, in operation, a syringe 36 and pressure jacket 38 are mounted to power head 22, so that the motor internal to power head 22 may be energized to move a plunger 37 within the barrel of syringe 36 toward and away from a discharge tip 40 of the syringe, to thereby expel fluid from the syringe 36 or fill the syringe with fluid. Pressure jacket 38 provides support to the outer walls of syringe 36 to protect the walls of syringe 36 from failure at high injection pressures.

Syringe 36 and pressure jacket 38 are made of a clear plastic material through which the operator can view the current location of plunger 37 and any fluid or air in the syringe between plunger 37 and discharge tip 40. Accordingly, as described above, an operator may tilt power head 22 upward, fill syringe 36 from a source of fluid while visually monitoring the filling process, then connect the injector to tubing leading to the patient, expel air from the tubing and syringe while visually monitoring the level of fluid in the syringe, and then once air has been expelled, tilt the injector downward and proceed to inject fluid into a subject.

To facilitate this filling process, and other operations that may be performed during injection of a subject, power head 22 includes the hand-operated movement control, which is in the form of the rotatable lever 29. Specifically, lever 29 is rotatable on an axis of rotation inside of power head 22. When the hand-operated control lever 29 is left in its home position, illustrated in FIG. 2, no plunger motion is generated by power head 22. However, when hand-operated control lever 29 is rotated toward syringe 36, forward plunger motion is generated by power head 22, expelling fluid or air from syringe 36. Alternatively, when hand-operated control lever 29 is rotated away from syringe 36, reverse plunger motion is generated by power head 22, filling syringe 36 with fluid or air.

To ensure that fluid injected into a subject is maintained at approximately body temperature, a heater blanket 42 is installed abutting the exterior wall of pressure jacket 38. Heater blanket 42 includes an electrical heater which generates heat for regulating the temperature of fluid within syringe 36. Heater blanket 42 is mounted to a post 44 extending from face plate 28, holding heater blanket 42 in thermal contact with pressure jacket 38.

At the rear end of power head 22 is an indicator lamp 46 (covered by a light-diffusing cover) which indicates the status of the power head.

Further details of exemplary hardware and software which control operation of an injector system such as that illustrated in FIGS. 1 and 2 can be found in U.S. Pat. No. 5,868,710 which is assigned to the assignee of the present invention and incorporated herein by reference, in its entirety.

Container Holder

One particular operational routine typically performed using an injector system is that of filling the syringe 36 with contrast media. This filling sequence for a power injector typically requires the use of both hands by the operator. A contrast container is held in one hand in close proximity to the injector while the other hand operates the injector controls to retract the plunger so as to fill the syringe. Even with injectors which can auto-fill a preset volume, the use of both hands by the operator is still required when initially starting the auto-fill sequence. Accordingly, a need exists to simplify the syringe sequence in power injectors so that an operator can have at least one hand available to perform other activities while filling a syringe.

In particular, one exemplary answer for addressing this need is utilization of a contrast container holder that attaches to a portion of the injector head 22 and secures the container in an orientation conducive to filling the syringe.

The material for this container holder can be any of a variety of suitable materials which are sufficiently rigid to support the weight of a typical contrast container. Preferable materials include plastics, stainless steel, aluminum and certain ceramics. Each of these materials can also withstand sufficient moisture, chemicals and temperature to easily permit cleaning of the holder by a variety of methods. Additionally, the material of the holder is such that it does not unreasonably contribute to breaking or damaging the contrast container but still functions in an environment in which it will likely receive numerous impacts of various severity.

Figure 3:
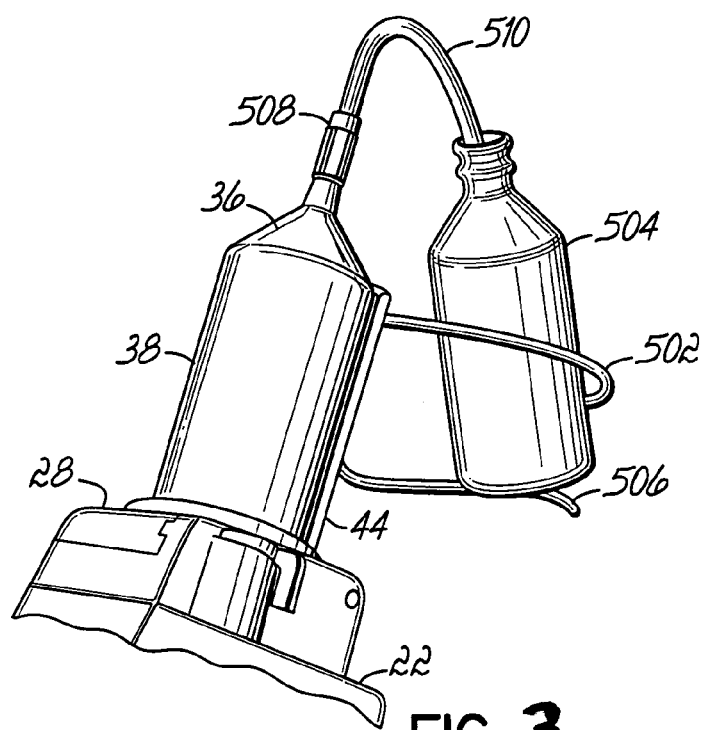
FIG. 3 illustrates a contrast container holder according to one embodiment of the present invention.

A particular exemplary design for a contrast container holder is illustrated in FIG. 3; however, one of ordinary skill would appreciate that other functionally equivalent designs are contemplated within the scope of the present invention. The container holder has a receptacle 502, 506 connected with a portion 44 of the injector housing and adapted for holding the contrast container 504 so that a fill tube 510 can easily reach the entire contrast container. More particularly, FIG. 3 illustrates a two piece container holder having an upper, curved arm 502 that curls around the contrast container 504 while a lower arm 506 supports the container 504 from underneath. The two arms 502 and 506 work in conjunction to hold the container 504 titled toward the injector head 22.

The exemplary holder 502, 506 features an open design that facilitates the securing and removing of a contrast container 504 using only one hand. While an operator can, of course, use two hands to insert and remove the container 504, it is not necessary. One hand operation is particularly useful when an operator must replace a container during a filling sequence.

Another feature of the holder 502, 506 is that it positions the container 504 in proximity to the syringe tip 508 so that a fill tube 510 can bridge from the syringe 36 to the bottom of the container 504. Typical fill tubes are 8 inches long but other lengths could be accommodated if desired.

Yet another feature of the contrast container holder 502, 506 is that it tilts the container 504 towards the fill tube 510 when the injector head 22 is appropriately oriented to perform a filling sequence. The previously incorporated U.S. Pat. No. 5,868,710 describes in detail one exemplary system for properly orienting an injector head during filling.

While a range of angles of tilt can be utilized for the holder 502, 506, the container can not be titled so much towards the injector head 22 that contrast fluid leaks out and neither can the tilt be so slight that it prevents the fill tube 510 from reaching the bottom of the container 504. If the fill tube 510 is unable to reach the bottom of the container 504, then the contrast fluid cannot be fully removed from the container 504.

Although FIG. 3 depicts the exemplary container holder 502, 506 attached to the heater jacket 44, the container holder 502, 506 can be coupled with the injector head 22 in a number of ways. For example, the holder can mount or clip on the underside of the injector head housing, or even the faceplate. Also, the holder can attach to the post which holds the heater blanket. In such an instance, the container holder installs on the injector similar to the manner in which the heater blanket attaches. In particular, through a slight interference fit, the holder can snap over a mounting post for convenient installation and permit tool-free removal for cleaning or other operating sequences of the injector that do not require the presence of a container. The holder can also be hinged such that it remains substantially permanently attached to the injector head but can fold out of the way so as to not interfere with other operating sequences or with storing the injector. The attachment of the container holder with the injector should allow tool-free attaching and removing so as not to further burden the operators with difficult and time-consuming tasks.

Figure 4:
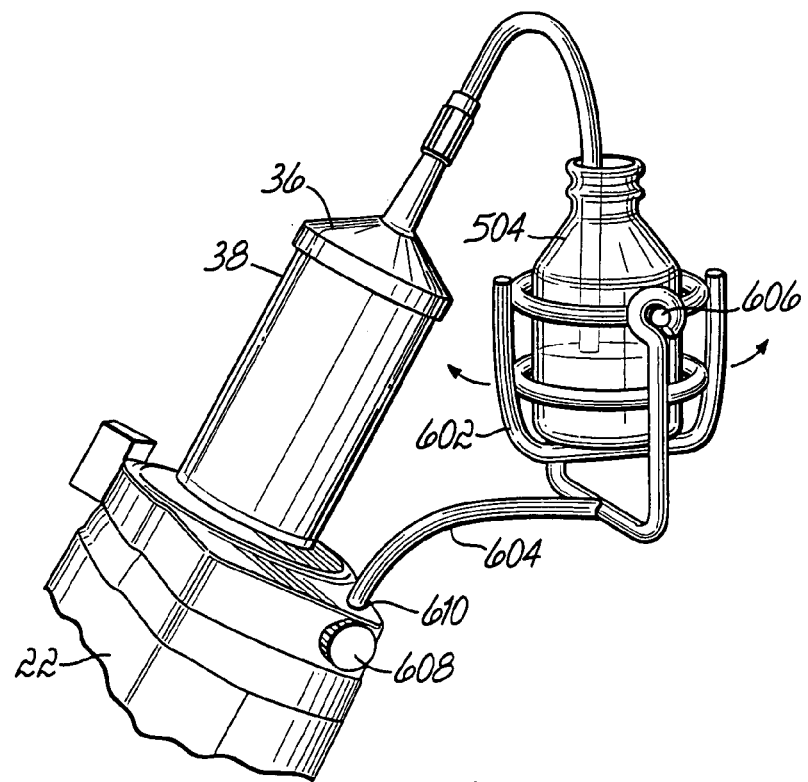
FIG. 4 illustrate a contrast container holder according to another embodiment of the present invention.

FIG. 4 illustrates an alternative embodiment, in which the container 504 is held in a cage 602. The cage is connected to a support arm 604 through hinges 606 (only one hinge is visible in this perspective view). The exemplary hinges 606 can be protrusions that loosely fit into an eye portion of the support arm 604. As the injector is rotated to orient it for filling, the hinges 606 ensure that the container 504 is properly oriented with respect to the injector head 22.

The support arm 604 can be adapted to fit within an opening 610 in the injector or its faceplate. To secure the support arm 604, a locking know 608 can be used that frictionally engages the support arm 604 within the opening 610, when tightened.

Figure 5:
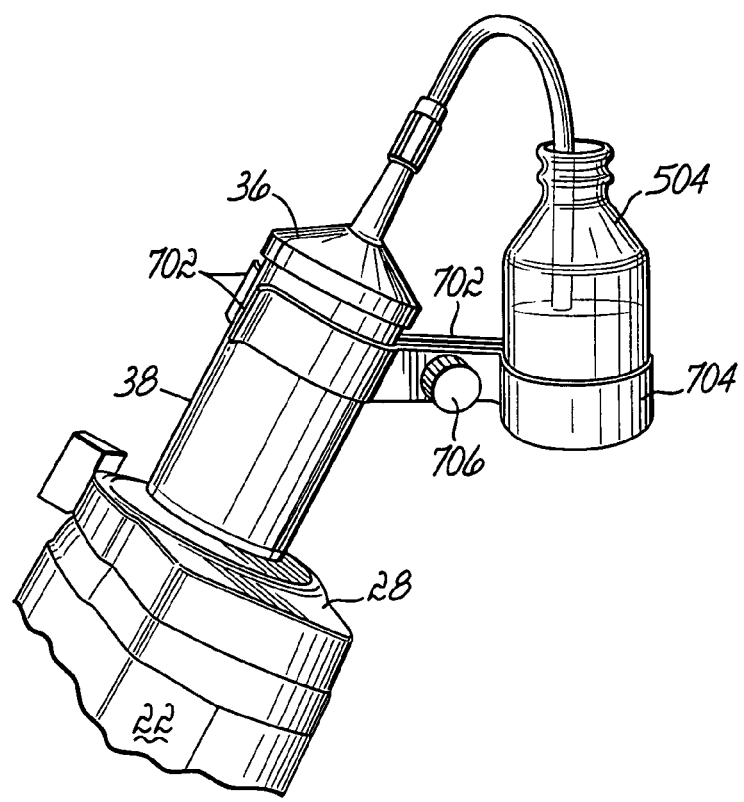
FIG. 5 illustrates a contrast container holder according to another embodiment of the present invention.

FIG. 5 illustrates a clamping alternative for holding the contrast container. According to this embodiment, the holder includes two semi-rigid arms 702 that fit around, for example, the pressure sleeve of the injector head 22. The holder also includes a basket portion 704 that is integrally formed with the arms 702 or otherwise attached thereto. By tightening the knob 706, the arms 702 are flexed inward and securely grip the pressure sleeve during the filling sequence.

Figure 6:
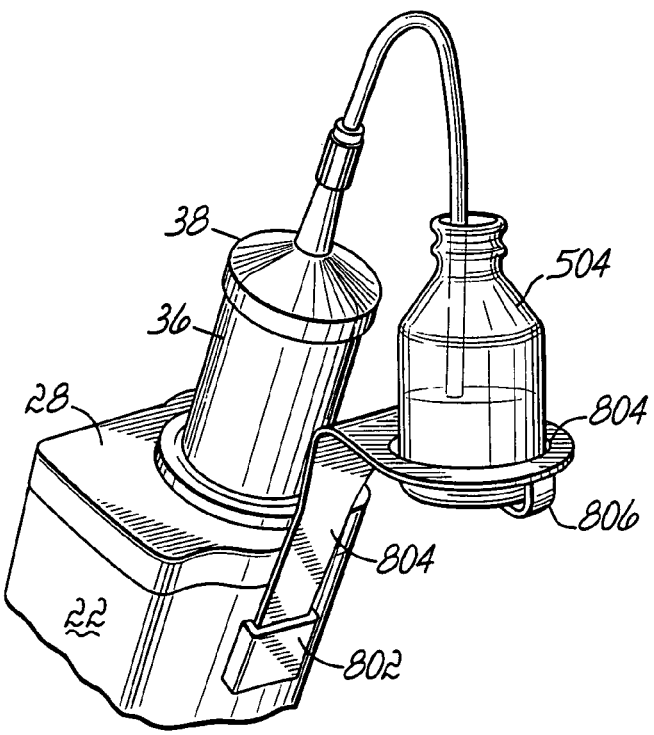
FIG. 6 illustrates a contrast container holder according to a further embodiment of the present invention.

FIG. 6 illustrates another type of removable container holder. This holder utilizes a bracket 802 that is affixed to the injector head housing 22. This bracket 802 can also be integrally formed with the housing during its manufacture. The holder includes an arm portion 804 that transitions to a circular opening 808 to hold the contrast container 504. A flange 806 is positioned under the circular opening 808 to prevent the container from falling through. The flange 806 could be annular or straight (as shown in the figure) and can reach fully across the opening 808 or only reach part of the way.

The above-described embodiments of the container holder illustrate a number of features which one of ordinary skill will readily recognize can be implemented in a number of functionally equivalent ways. Thus, these embodiments are presented as examples and are not intended to limit the present invention to only the specific forms shown.

Filling Sequence

Occasionally when filling a syringe, the filling sequence can be problematic in that if it is performed too fast, the contrast media is aerated or if it is performed too slow, the sequence can take an unreasonable amount of time to complete. When filling a syringe, operators try to perform the filling at a maximum filling rate for contrast media that will avoid aerating the contrast media. This rate is partly dependent on the contrast media, its viscosity and the possible presence of air in the fill tube. While this speed can be programmed in the injector and automatically used, an operator typically monitors the syringe filling to further reduce the likelihood of aeration of the contrast media. A need exists for a filling sequence that permits filling of the syringe with contrast fluid faster than the maximum filling speed attainable when air is in the fill tube.

Figure 7:
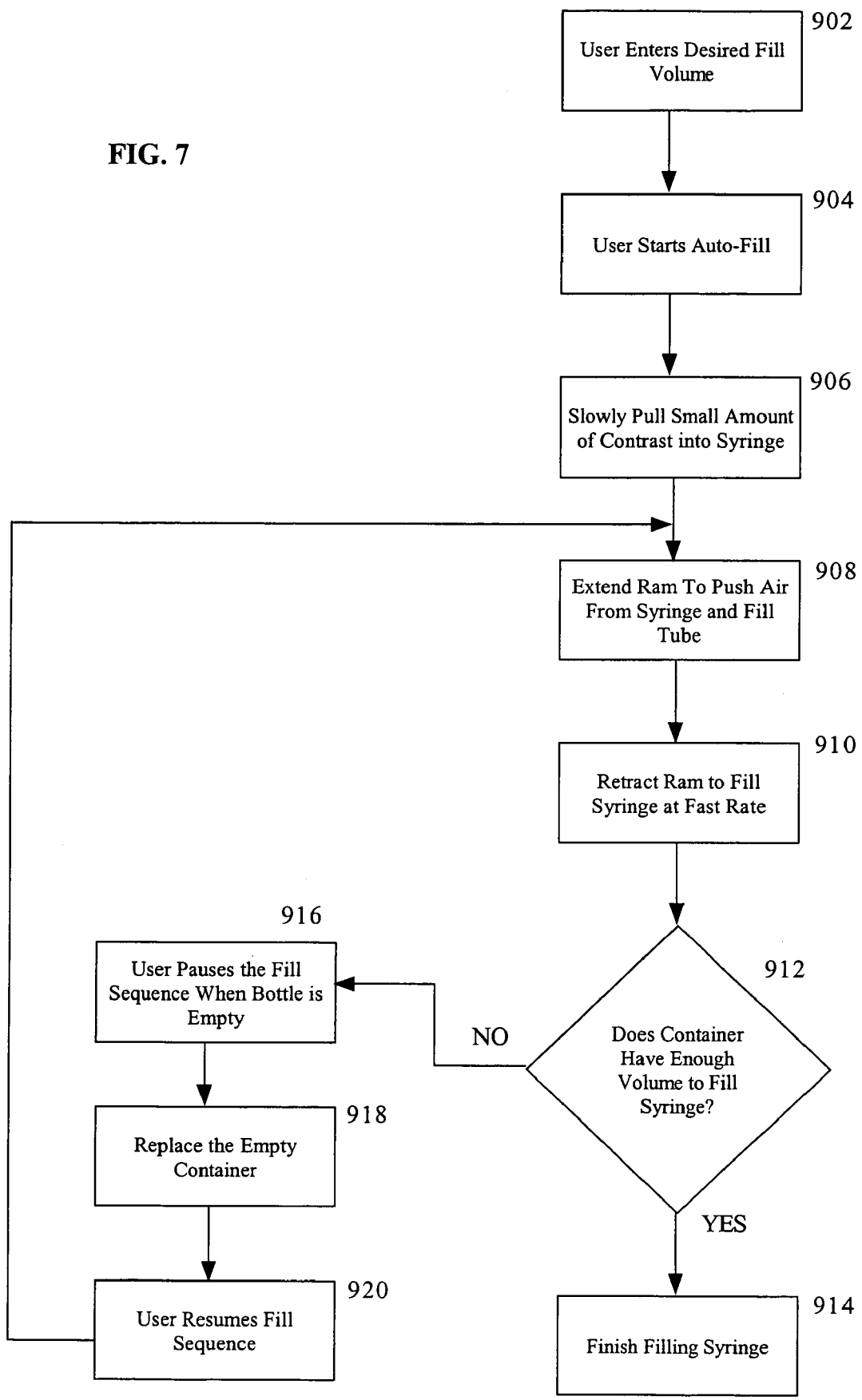
FIG. 7 illustrates a flowchart of an exemplary method for filling a syringe using an injector system.

One exemplary automatic filling sequence is illustrated as a flowchart in FIG. 7. Of course, a user could perform a manual filling sequence as well without deviating from the scope of the present invention. The first step in an automatic filling sequence, step 902, is to enter a desired fill volume. Once this value is entered, the user can initiate, in step 904, the start of the auto-fill sequence. In response, the injector system will slowly pull, in step 906, a small volume of contrast into the syringe while the syringe is pointing substantially upwards. An injector head that is oriented so as to have the syringe positioned above the opposite end of the head and to be tilted 45 degrees or less from vertical is considered to be pointing substantially upwards; however, a tilt angle less than 20 degrees is preferable. The small volume of contrast fluid that is pulled into the syringe at a slow enough rate so as not to aerate the fluid is a volume sufficient to be visibly noticed by the operator performing the filling sequence and is usually at least 20 ml.

Once the small volume of contrast is in the syringe, the injector system automatically (or the operator, manually) reverses the direction of the injector ram, in step 908, so that the contrast fluid is expelled from the syringe. In particular, the ram is operated such that at least a portion of the fluid in the syringe travels through the fill tube and re-enters the contrast container. Thus, all air is expelled from the fill tube and syringe.

With no air in the syringe and fill tube, the injector system can energize the ram, in step 910, to pull back the programmed volume with a reduced risk of introducing bubbles due to aeration. The rate at which the contrast media can now be pulled back is faster than if the air had not been previously expelled from the fill tube and syringe as in step 908.

A similar technique can be used to change bottles of contrast media during a filling sequence when the contrast remaining in a container is insufficient to provide the volume of contrast media needed to correctly fill a syringe. This technique is illustrated as steps 912-920 of the flowchart of FIG. 7. This technique is useful by itself as a way to change contrast containers during a filling sequence or can be part of an automatic filling sequence as shown in FIG. 7.

During filling, the contrast container may be emptied, in step 912, and air introduced into the fill tube while acquiring the final amount from the container. When the container is empty, the operator can pause the filling sequence, in step 916, using the operator interface of the injector system. As a result of the operator pausing the filling sequence, the ram is stopped so that the empty container can be replaced in step 918 with a new container having contrast media.

The fill sequence can then be restarted in step 920 by the operator. Upon restart, the ram automatically operates in the opposite direction to push air out of the fill tube and syringe. Expulsion of all air from the system, in step 908, is ensured by operating the ram in this direction until contrast fluid from the syringe re-enters the new container. Once all the air is expunged, the ram direction can be reversed to pull up the contrast media, in step 910, so as to fill the syringe. The rate at which the contrast media can now be pulled back is faster than if the air had not been expunged. With the new contrast container available the filling of the syringe can be completed in step 914.

Although the description of the flowchart of FIG. 7 includes the interaction of an operator in many steps, these processes can be automated by appropriate programming of the injector system to perform the steps without requiring the intervention of an operator. In order to program the injector system in this way, assumptions will be made about the volumetric capacity of the fill tube used between the syringe and the contrast container. Knowing this volumetric capacity will allow an automatic routine to draw enough contrast media so that a small amount reaches the syringe and to reverse the ram for a time and speed sufficient to expel contrast media to ensure all the air is successfully expunged from both the syringe and the fill tube.

Additionally, the routine of FIG. 7 can be automated such that when the operator has replaced the contrast container and instructs the injector system to continue or resume the filling sequence, the injector can control the ram direction and speed to automatically expel sufficient media to ensure the fill tube is cleared of air and then automatically reverse the ram so as to draw more contrast media in at the faster rate.

While the present invention has been illustrated by description of various embodiments and while these embodiments have been described in considerable detail, it is not the intention of the applicant to restrict or in any way limit the scope of the claims to such detail. Additional advantages and modifications will readily appear to those skilled in the art. The invention in its broader aspect is, therefore, not limited to the specific details, representative system, apparatus, and method, and illustrative example shown and described. Accordingly, departures may be made from such details without departing from the spirit or scope of the applicant's general inventive concept.

What is claimed is:

1. A method for performing a filling sequence in a contrast media injector system that uses a fill tube coupling a syringe to contrast media supply to fill the syringe with a desired fill volume of contrast media, the method comprising:
   attaching said fill tube to said syringe;
   drawing contrast media into the syringe through the fill tube at a first fill rate;
   thereafter, automatically expelling substantially all air from the fill tube by automatically reversing the first fill rate and expelling fluid from said syringe, wherein at least some of the contrast media is expelled through the fill tube during the expelling;
   thereafter, filling the syringe at a second fill rate to fill the syringe with the desired fill volume of contrast media, wherein the second fill rate is faster than the first fill rate; and
   thereafter, injecting contrast media into a patient.

2. The method according to claim 1 wherein the drawing comprises drawing a first amount of contrast media into the syringe, and the expelling comprises expelling substantially all of the first amount of contrast media out of the syringe.

3. The method according to claim 1, wherein the expelling comprises expelling substantially all air from the syringe.

4. The method according to claim 1, wherein the expelling is performed by the contrast media injector automatically under control of control circuitry of the injector.

5. The method according to claim 1, wherein the filling is performed by the contrast media injector automatically under control of control circuitry of the injector.

6. The method according to claim 1, wherein the expelling and the filling are performed by the contrast media injector automatically under control of control circuitry of the injector.

7. The method of claim 1, wherein the syringe is oriented such that a discharge tip of the syringe is positioned above a barrel of the syringe during the drawing, the expelling, and the filling.

8. The method of claim 1, wherein both air and contrast media are expelled through a discharge tip of the syringe during the expelling.

9. A method for changing contrast media containers during a syringe filling sequence, the method comprising:
   attaching a fill tube to a syringe;
   thereafter, filling a syringe at at least one of a first fill rate and a second fill rate through the fill tube, the fill tube coupled between the syringe and a first contrast container;
   thereafter, pausing the filling when the first contrast container is substantially emptied;
   thereafter, replacing the first contrast container with a second contrast container;
   thereafter, coupling the fill tube between the syringe and the second contrast container;
   thereafter, expelling substantially all air from the fill tube coupled between the syringe and the second contrast container wherein at least some of the contrast media is expelled from the syringe, through the fill tube, and into the second contrast container during the expelling; and
   thereafter, resuming filling the syringe from the second contrast container at the second fill rate that is faster than the first fill rate.

10. The method according to claim 9 wherein the step of expelling comprises:
   expelling a portion of contrast media that was acquired from the first contrast container out of the syringe through the fill tube and into the second contrast container.

11. The method according to claim 9, wherein the expelling comprises expelling substantially all air from the syringe.

12. The method of claim 9, wherein the syringe is oriented such that a discharge tip of the syringe is positioned above a barrel of the syringe during the filling, the expelling, and the resuming.

13. The method of claim 9, wherein both air and contrast media are expelled through a discharge tip of the syringe during the expelling.

14. A method of operation for a contrast media injector system, the method comprising:
   automatically drawing an initial volume of medical fluid into a syringe of a contrast media injector system at a first fill rate;
   after the drawing, automatically ceasing drawing and commencing expelling at least some of the medical fluid from the syringe; and
   thereafter, automatically ceasing expelling and commencing filling the syringe at a second fill rate that is faster than the first fill rate, wherein a total volume of medical fluid in the syringe after the filling is greater than the initial volume.

15. The method of claim 14, wherein the first fill rate is a rate sufficient to avoid aeration of the medical fluid.

16. The method of claim 14, wherein the drawing comprises drawing at least 20 ml of the medical fluid into the syringe.

17. The method of claim 14, wherein the drawing comprises drawing medical fluid through a fill tube and into the syringe.

18. The method of claim 14, wherein the syringe is oriented such that a discharge tip of the syringe is positioned above a barrel of the syringe during the drawing, the expelling, and the filling.

19. The method of claim 14, wherein both air and contrast media are expelled through a discharge tip of the syringe during the expelling.

20. A method of performing an automated syringe filling sequence in a contrast media injector, the method comprising:
   the injector pulling a first amount of fluid into a syringe of the injector at a first rate;
      after the injector pulling the first amount of fluid into the syringe, the injector automatically reversing a direction of a ram of the injector to expel at least a portion of the fluid from the syringe; and
      after the injector automatically reversing the direction of the ram, the injector automatically retracting the ram at a second rate faster than the first rate to draw a second volume of the fluid into the syringe.

21. The method of claim 20, wherein the first rate is slow enough so as not to aerate the fluid.

22. The method of claim 21, wherein the first volume is a volume sufficient to be visibly noticed by an operator of the injector.

23. The method of claim 22, wherein the first volume is at least about 20 ml.

24. The method of claim 23, wherein all air is expelled from the syringe upon completion of the injector automatically reversing the direction of the ram to expel at least a portion of the fluid from the syringe.

25. The method of claim 24, wherein a volume of fluid in the syringe upon completion of the injector automatically retracting the ram is a desired fill volume entered into the injector by an operator of the injector prior to the injector pulling the first amount of fluid into the syringe.

26. The method of claim 25, wherein the injector is designed such that the syringe is pointing substantially upward during:
   the injector pulling the first amount of the fluid into the syringe;
      the injector automatically reversing the direction of the ram; and
      the injector automatically retracting the ram.

27. The method of claim 23, wherein a volume of fluid in the syringe upon completion of the injector automatically retracting the ram is a desired fill volume entered into the injector by an operator of the injector prior to the injector pulling the first amount of fluid into the syringe.

28. The method of claim 27, wherein the injector is designed such that the syringe is pointing substantially upward during:
   the injector pulling the first amount of the fluid into the syringe;
      the injector automatically reversing the direction of the ram; and
      the injector automatically retracting the ram.

29. The method of claim 23, wherein the injector is designed such that the syringe is pointing substantially upward during:
   the injector pulling the first amount of the fluid into the syringe;
      the injector automatically reversing the direction of the ram; and
      the injector automatically retracting the ram.

30. The method of claim 22, wherein all air is expelled from the syringe upon completion of the injector automatically reversing the direction of the ram to expel at least a portion of the fluid from the syringe.

31. The method of claim 30, wherein a volume of fluid in the syringe upon completion of the injector automatically retracting the ram is a desired fill volume entered into the injector by an operator of the injector prior to the injector pulling the first amount of fluid into the syringe.

32. The method of claim 31, wherein the injector is designed such that the syringe is pointing substantially upward during:
   the injector pulling the first amount of the fluid into the syringe;
      the injector automatically reversing the direction of the ram; and
      the injector automatically retracting the ram.

33. The method of claim 30, wherein the injector is designed such that the syringe is pointing substantially upward during:
   the injector pulling the first amount of the fluid into the syringe;
      the injector automatically reversing the direction of the ram; and
      the injector automatically retracting the ram.

34. The method of claim 22, wherein a volume of fluid in the syringe upon completion of the injector automatically retracting the ram is a desired fill volume entered into the injector by an operator of the injector prior to the injector pulling the first amount of fluid into the syringe.

35. The method of claim 34, wherein the injector is designed such that the syringe is pointing substantially upward during:
   the injector pulling the first amount of the fluid into the syringe;
      the injector automatically reversing the direction of the ram; and
      the injector automatically retracting the ram.

36. The method of claim 22, wherein the injector is designed such that the syringe is pointing substantially upward during:
   the injector pulling the first amount of the fluid into the syringe;
      the injector automatically reversing the direction of the ram; and
      the injector automatically retracting the ram.

37. The method of claim 21, wherein the first volume is at least about 20 ml.

38. The method of claim 37, wherein all air is expelled from the syringe upon completion of the injector automatically reversing the direction of the ram to expel at least a portion of the fluid from the syringe.

39. The method of claim 38, wherein a volume of fluid in the syringe upon completion of the injector automatically retracting the ram is a desired fill volume entered into the injector by an operator of the injector prior to the injector pulling the first amount of fluid into the syringe.

40. The method of claim 39, wherein the injector is designed such that the syringe is pointing substantially upward during:
   the injector pulling the first amount of the fluid into the syringe;
   the injector automatically reversing the direction of the ram; and
   the injector automatically retracting the ram.

41. The method of claim 38, wherein the injector is designed such that the syringe is pointing substantially upward during:
   the injector pulling the first amount of the fluid into the syringe;
   the injector automatically reversing the direction of the ram; and
   the injector automatically retracting the ram.

42. The method of claim 37, wherein a volume of fluid in the syringe upon completion of the injector automatically retracting the ram is a desired fill volume entered into the injector by an operator of the injector prior to the injector pulling the first amount of fluid into the syringe.

43. The method of claim 42, wherein the injector is designed such that the syringe is pointing substantially upward during:
   the injector pulling the first amount of the fluid into the syringe;
   the injector automatically reversing the direction of the ram; and
   the injector automatically retracting the ram.

44. The method of claim 37, wherein the injector is designed such that the syringe is pointing substantially upward during:
   the injector pulling the first amount of the fluid into the syringe;
   the injector automatically reversing the direction of the ram; and
   the injector automatically retracting the ram.

45. The method of claim 21, wherein all air is expelled from the syringe upon completion of the injector automatically reversing the direction of the ram to expel at least a portion of the fluid from the syringe.

46. The method of claim 45, wherein a volume of fluid in the syringe upon completion of the injector automatically retracting the ram is a desired fill volume entered into the injector by an operator of the injector prior to the injector pulling the first amount of fluid into the syringe.

47. The method of claim 46, wherein the injector is designed such that the syringe is pointing substantially upward during:
   the injector pulling the first amount of the fluid into the syringe;
   the injector automatically reversing the direction of the ram; and
   the injector automatically retracting the ram.

48. The method of claim 24, wherein the injector is designed such that the syringe is pointing substantially upward during:
   the injector pulling the first amount of the fluid into the syringe;
   the injector automatically reversing the direction of the ram; and
   the injector automatically retracting the ram.

49. The method of claim 45, wherein the injector is designed such that the syringe is pointing substantially upward during:
   the injector pulling the first amount of the fluid into the syringe;
   the injector automatically reversing the direction of the ram; and
   the injector automatically retracting the ram.

50. The method of claim 21, wherein a volume of fluid in the syringe upon completion of the injector automatically retracting the ram is a desired fill volume entered into the injector by an operator of the injector prior to the injector pulling the first amount of fluid into the syringe.

51. The method of claim 50, wherein the injector is designed such that the syringe is pointing substantially upward during:
   the injector pulling the first amount of the fluid into the syringe;
   the injector automatically reversing the direction of the ram; and
   the injector automatically retracting the ram.

52. The method of claim 21, wherein the injector is designed such that the syringe is pointing substantially upward during:
   the injector pulling the first amount of the fluid into the syringe;
   the injector automatically reversing the direction of the ram; and
   the injector automatically retracting the ram.

53. The method of claim 20, wherein the first volume is at least about 20 ml.

54. The method of claim 53, wherein all air is expelled from the syringe upon completion of the injector automatically reversing the direction of the ram to expel at least a portion of the fluid from the syringe.

55. The method of claim 54, wherein a volume of fluid in the syringe upon completion of the injector automatically retracting the ram is a desired fill volume entered into the injector by an operator of the injector prior to the injector pulling the first amount of fluid into the syringe.

56. The method of claim 55, wherein the injector is designed such that the syringe is pointing substantially upward during:
   the injector pulling the first amount of the fluid into the syringe;
   the injector automatically reversing the direction of the ram; and
   the injector automatically retracting the ram.

57. The method of claim 54, wherein the injector is designed such that the syringe is pointing substantially upward during:
   the injector pulling the first amount of the fluid into the syringe;
   the injector automatically reversing the direction of the ram; and
   the injector automatically retracting the ram.

58. The method of claim 53, wherein a volume of fluid in the syringe upon completion of the injector automatically retracting the ram is a desired fill volume entered into the injector by an operator of the injector prior to the injector pulling the first amount of fluid into the syringe.

59. The method of claim 58, wherein the injector is designed such that the syringe is pointing substantially upward during:
the injector pulling the first amount of the fluid into the syringe;
the injector automatically reversing the direction of the ram; and
the injector automatically retracting the ram.

60. The method of claim 53, wherein the injector is designed such that the syringe is pointing substantially upward during:
the injector pulling the first amount of the fluid into the syringe;
the injector automatically reversing the direction of the ram; and
the injector automatically retracting the ram.

61. The method of claim 20, wherein the first volume is a volume sufficient to be visibly noticed by an operator of the injector.

62. The method of claim 61, wherein the first volume is at least about 20 ml.

63. The method of claim 62, wherein all air is expelled from the syringe upon completion of the injector automatically reversing the direction of the ram to expel at least a portion of the fluid from the syringe.

64. The method of claim 63, wherein a volume of fluid in the syringe upon completion of the injector automatically retracting the ram is a desired fill volume entered into the injector by an operator of the injector prior to the injector pulling the first amount of fluid into the syringe.

65. The method of claim 64, wherein the injector is designed such that the syringe is pointing substantially upward during:
the injector pulling the first amount of the fluid into the syringe;
the injector automatically reversing the direction of the ram; and
the injector automatically retracting the ram.

66. The method of claim 63, wherein the injector is designed such that the syringe is pointing substantially upward during:
the injector pulling the first amount of the fluid into the syringe;
the injector automatically reversing the direction of the ram; and
the injector automatically retracting the ram.

67. The method of claim 62, wherein a volume of fluid in the syringe upon completion of the injector automatically retracting the ram is a desired fill volume entered into the injector by an operator of the injector prior to the injector pulling the first amount of fluid into the syringe.

68. The method of claim 67, wherein the injector is designed such that the syringe is pointing substantially upward during:
the injector pulling the first amount of the fluid into the syringe;
the injector automatically reversing the direction of the ram; and
the injector automatically retracting the ram.

69. The method of claim 62, wherein the injector is designed such that the syringe is pointing substantially upward during:
the injector pulling the first amount of the fluid into the syringe;
the injector automatically reversing the direction of the ram; and
the injector automatically retracting the ram.

70. The method of claim 61, wherein all air is expelled from the syringe upon completion of the injector automatically reversing the direction of the ram to expel at least a portion of the fluid from the syringe.

71. The method of claim 70, wherein a volume of fluid in the syringe upon completion of the injector automatically retracting the ram is a desired fill volume entered into the injector by an operator of the injector prior to the injector pulling the first amount of fluid into the syringe.

72. The method of claim 71, wherein the injector is designed such that the syringe is pointing substantially upward during:
the injector pulling the first amount of the fluid into the syringe;
the injector automatically reversing the direction of the ram; and
the injector automatically retracting the ram.

73. The method of claim 70, wherein the injector is designed such that the syringe is pointing substantially upward during:
the injector pulling the first amount of the fluid into the syringe;
the injector automatically reversing the direction of the ram; and
the injector automatically retracting the ram.

74. The method of claim 61, wherein a volume of fluid in the syringe upon completion of the injector automatically retracting the ram is a desired fill volume entered into the injector by an operator of the injector prior to the injector pulling the first amount of fluid into the syringe.

75. The method of claim 66, wherein the injector is designed such that the syringe is pointing substantially upward during:
the injector pulling the first amount of the fluid into the syringe;
the injector automatically reversing the direction of the ram; and
the injector automatically retracting the ram.

76. The method of claim 61, wherein the injector is designed such that the syringe is pointing substantially upward during:
the injector pulling the first amount of the fluid into the syringe;
the injector automatically reversing the direction of the ram; and
the injector automatically retracting the ram.

77. The method of claim 20, wherein all air is expelled from the syringe upon completion of the injector automatically reversing the direction of the ram to expel at least a portion of the fluid from the syringe.

78. The method of claim 77, wherein a volume of fluid in the syringe upon completion of the injector automatically retracting the ram is a desired fill volume entered into the injector by an operator of the injector prior to the injector pulling the first amount of fluid into the syringe.

79. The method of claim 78, wherein the injector is designed such that the syringe is pointing substantially upward during:
the injector pulling the first amount of the fluid into the syringe;
the injector automatically reversing the direction of the ram; and
the injector automatically retracting the ram.

80. The method of claim 77, wherein the injector is designed such that the syringe is pointing substantially upward during:
the injector pulling the first amount of the fluid into the syringe;
the injector automatically reversing the direction of the ram; and
the injector automatically retracting the ram.

81. The method of claim 20, wherein a volume of fluid in the syringe upon completion of the injector automatically retracting the ram is a desired fill volume entered into the injector by an operator of the injector prior to the injector pulling the first amount of fluid into the syringe.

82. The method of claim 81, wherein the injector is designed such that the syringe is pointing substantially upward during:
the injector pulling the first amount of the fluid into the syringe;
the injector automatically reversing the direction of the ram; and
the injector automatically retracting the ram.

83. The method of claim 20, wherein the injector is designed such that the syringe is pointing substantially upward during:
the injector pulling the first amount of the fluid into the syringe;
the injector automatically reversing the direction of the ram; and
the injector automatically retracting the ram.

* * * * *

UNITED STATES PATENT AND TRADEMARK OFFICE
CERTIFICATE OF CORRECTION

PATENT NO. : 7,621,892 B2
APPLICATION NO. : 10/750427
DATED : November 24, 2009
INVENTOR(S) : Fago et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 668 days.

Signed and Sealed this

Twenty-sixth Day of October, 2010

David J. Kappos
*Director of the United States Patent and Trademark Office*